United States Patent [19]

Birchak et al.

[11] Patent Number: 4,571,693
[45] Date of Patent: Feb. 18, 1986

[54] ACOUSTIC DEVICE FOR MEASURING FLUID PROPERTIES

[75] Inventors: James R. Birchak, Spring; Edward A. Lygas, Houston, both of Tex.

[73] Assignee: NL Industries, Inc., New York, N.Y.

[21] Appl. No.: 473,811

[22] Filed: Mar. 9, 1983

[51] Int. Cl.⁴ ............................................. G01T 1/16
[52] U.S. Cl. ..................................... 364/509; 73/151; 73/24; 364/558; 364/422
[58] Field of Search ....................... 364/509, 422, 558; 73/151, 32 A, 24; 367/140, 35, 157, 912, 141, 142, 151, 903

[56] References Cited

U.S. PATENT DOCUMENTS

| | | | |
|---|---|---|---|
| 3,357,246 | 12/1967 | Stearn et al. | 73/290 V |
| 3,590,228 | 6/1971 | Burke | 364/422 |
| 3,631,385 | 11/1971 | Silverman | 367/35 X |
| 3,776,032 | 12/1973 | Vogel | 73/155 |
| 3,858,037 | 12/1974 | Moore et al. | 364/422 |
| 4,144,517 | 3/1979 | Baumoel | 73/290 V X |
| 4,203,324 | 5/1980 | Baumoel | 73/290 V |
| 4,210,965 | 7/1980 | Ingram | 364/422 X |
| 4,255,798 | 3/1981 | Havira | 367/73 |
| 4,280,823 | 7/1981 | Szonntagh | 73/24 X |
| 4,323,991 | 4/1982 | Holmes et al. | 367/912 X |
| 4,328,567 | 5/1982 | Dodge | 364/422 |
| 4,405,988 | 9/1983 | Forster et al. | 364/509 X |
| 4,413,516 | 11/1983 | Croom, Jr. et al. | 73/151 X |

Primary Examiner—Edward J. Wise
Attorney, Agent, or Firm—Browning, Bushman, Zamecki & Anderson

[57] ABSTRACT

An apparatus and method for measuring fluid characteristics, particularly useful in performing measurements in remote and severe environments is disclosed. The probe employs an ultrasonic transmitter and receiver, preferably a unitary ultrasonic transducer to both transmit and receive the ultrasonic signal. Further, the probe includes an internal reference reflecting surface hermetically sealed from contact with the fluid and one or more solid/fluid reflecting surfaces as are required. Preferably, two solid/fluid reflecting surfaces are located on opposite sides of a fluid receiving gap. The apparatus and method are useful in measuring fluid characteristics both at remote surface and in downhole drilling locations.

21 Claims, 3 Drawing Figures

ACOUSTIC DEVICE FOR MEASURING FLUID PROPERTIES

BACKGROUND OF THE INVENTION

1. Field of the Invention

The present invention relates to an apparatus and method for measuring fluid characteristics. More particularly, a device, including an integral reflecting means to provide an internal reference signal, useful in measuring fluid characteristics such as density, compressibility, acoustic impedance and attenuation is disclosed. A device constructed in accordance with the present invention is particularly useful for the remote monitoring of these characteristics, and is advantageously incorporated into a drill collar or the like for downhole applications.

2. Description of the Background

The measurement of various fluid characteristics in static and dynamic environments is quite important in many industrial processes. Such characteristics as the density, compressibility, acoustic impedance and attenuation of a fluid may contain important information for the system operator. Of particular interest in many applications is the determination of fluid density. Typically, to make a density measurement of a fluid, an accurate volumetric or dimensional measurement is required. However, for rapid or remote monitoring and particularly in dynamic situations, a simplified approach is desired. A probe which may be inserted within a flowing stream to measure these fluid characteristics without requiring flow interruption or volumetric measurement is desired.

Ultrasonic devices have been developed which are capable of providing some information concerning fluids in some circumstances. For example, devices using ultrasonic signals to determine the fluid level in containers are disclosed in U.S. Pat. Nos. 3,357,246, 4,144,517 and 4,203,324.

Determination of various fluid characteristics, particularly the density of the drilling fluid, is important during rotary drilling operations to prevent blowouts. In these operations, a drilling fluid, commonly referred to as drilling mud, is normally pumped down the drill string, exited through the drill bit and returned to the surface through the annulus formed between the drill string and the well bore. As the bit passes into and through various fluid containing zones, these fluids will enter the borehole if the pressure in the zone is greater than the pressure in the borehole. Lightweight fluids, e.g., salt water, light hydrocarbons and particularly gases, entering the borehole, decrease the density of the drilling fluid. Because the total weight of fluid within the borehole is critical to maintaining sufficient pressure to prevent blowouts when high pressure zones are entered, the remote determination of the density of the drilling fluid is extremely important.

U.S. Pat. No. 3,776,032 discloses a method and apparatus for detecting the inflow of fluid into a well during rotary drilling. This apparatus comprises a pair of acoustical transducers for transmitting high frequency voltage energy into the drilling fluid near the drill bit. The difference in the density of the fluid within the drill string near the drill bit and of the fluid within the annulus is determined. This difference or relative density is transmitted to the surface to indicate the influx of material into the borehole having a density different from that of the initial drilling fluid. This technique, while providing relative information, does not provide an absolute measurement of the density, compressibility, viscosity, acoustic impedance or attenuation of the fluid in the borehole. While this device and method provides a means of determining relative densities, it does not provide a device, including an internal referencing means, for making absolute measurements.

The device and method of the present invention overcome many of the disadvantages of the prior systems and provide a device useful for making accurate, remote measurements of fluid characteristics in a static or dynamic environment. This device and method are particularly useful in making measurements of fluid characteristics, e.g., the density of the drilling mud, at a remote downhole location during drilling. The knowledge of these characteristics permits the drilling rig operator to responsibly alter the characteristics of the drilling mud when required to maintain the desired density and to prevent the development of potential blowout conditions.

The art has long sought a simple device having an internal reference for measuring density and other fluid characteristics at remote locations in static and dynamic operations.

SUMMARY OF THE INVENTION

The present invention provides an apparatus and method for measuring fluid characteristics in both static and dynamic conditions at remote locations. The device comprises a solid probe body for contact with means for transmitting ultrasonic signals, means for receiving ultrasonic signals and the fluid whose characteristics are to be determined. The device includes means for transmitting and receiving ultrasonic signals through the probe body. In a preferred embodiment, a single ultrasonic transducer functions as both the transmitting and receiving means. The device further includes a first surface for contacting the fluid and for providing a first solid/fluid interface to produce a first reflected ultrasonic fluid signal. Preferably, this first surface is substantially flat and substantially perpendicular to the direction of propagation of the ultrasonic signal.

Further, the device includes a means sealed from contact with the fluid and within the solid probe body for reflecting a portion of the ultrasonic signal to provide a reflected ultrasonic reference signal. This referencing means is conveniently provided by a void within the probe. Preferably, the surface of the void proximal to the transmitting/receiving means is substantially flat and substantially perpendicular to the direction of propagation of the ultrasonic wave. Alternatively, the void may be filled with a material having a different density from that of the probe to provide the desired reflecting surface.

In another embodiment of the present invention, the probe includes a second surface for contacting the fluid to provide a second solid/fluid interface to produce a second reflected ultrasonic fluid signal. Preferably, this second surface is substantially parallel to the first fluid contacting surface to form a gap therebetween. The fluid whose characteristics are to be determined is received in this gap under either static or dynamic conditions. The distance between the transmitting/receiving means and the referencing means and the distance between the first and second fluid contacting surfaces are preferably chosen to limit receiver interference from secondary and high order relected waves.

The present invention further contemplates means for gating the received, reflected ultrasonic signals and measuring the magnitude of the first half-cycle thereof, together with the travel time of the signals through the fluid between the first and second fluid reflecting surfaces.

The method of the present invention comprises contacting a fluid with a device constructed in accordance with the present disclosure, transmitting ultrasonic signals therethrough and receiving ultrasonic signals reflected from an internal reference reflecting means and from one or more solid/fluid interfaces. The present method further contemplates gating the received signals and measuring the amplitudes of the reflected signals and optionally the travel time through the fluid.

These and other meritorious features and advantages of the present invention will be more fully appreciated from the following detailed description and claims.

BRIEF DESCRIPTION OF THE DRAWINGS

Other features and intended advantages of the invention will be more readily apparent by reference to the following detailed description in connection with the accompanying drawings wherein.

While the invention will be described in connection with a presently preferred embodiment, it will be understood that it is not intended to limit the invention to that embodiment. On the contrary, it is intended to cover all alternatives, modifications and equivalents as may be included within the spirit of the invention as defined in the appended claims.

DETAILED DESCRIPTION OF THE PREFERRED EMBODIMENT

Figure 1:
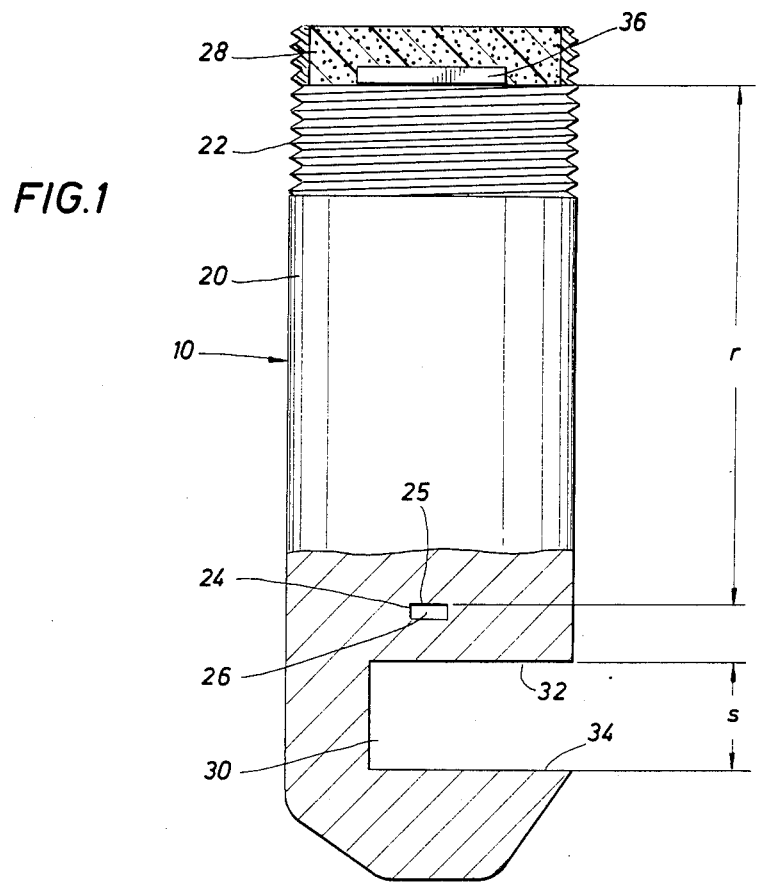
FIG. 1 is a cross-sectional representation of a device in accordance with the present invention useful for measuring fluid characteristics.

Referring now to FIG. 1, there is illustrated a simple embodiment of a probe 10 suitable for measuring fluid characteristics in accordance with the teachings of the present invention. Illustrated probe 10 comprises a solid probe body 20 constructed of a material suitable for transmitting ultrasonic signals of the desired frequency. Further, it is preferred that this material be resistant to high temperatures and corrosive materials. Probe body 20 is conveniently constructed of aluminum, magnesium or a suitable plastic material useful in the environmental conditions to which the probe will be subjected. In a particular preferred embodiment it is desired that such a probe be constructed of materials resistant to the conditions found in deep boreholes in drilling for oil and gas. Such a probe may be constructed of steel or may even be formed as a unitary portion of or as an insert in a drill collar.

In the embodiment illustrated in FIG. 1, probe 10 is threaded at one end 22 for engagement with a supporting body (not illustrated) such as the interior of a tank, pipe or other vessel or conduit. Probe 10 is also adapted for inclusion on the interior or exterior of a drill string member. A suitable absorbing material 28, e.g., a tungsten loaded epoxy or lead balls, backs transducer 36. Solid probe body 20 may be further surrounded except at its solid/fluid interfaces with an absorbing material (not shown) such as rubber to minimize transmission and reception of ultrasonic signals outside probe body 20.

Probe 10 further includes a means for generating and transmitting an ultrasonic signal. Appropriate means include ultrasonic transducer 36 placed in contact with a surface of probe body 20. A disc of any suitable piezoelectric material, e.g., lead zirconate, quartz, barium titanate, a Rochelle salt or ammonium dihydrogen phosphate, which produces an ultrasonic signal in the desired frequency range and is useful in the environmental conditions to which the probe will be subjected conveniently forms transducer 36. The ultrasonic signal is stimulated by pulser 40 and accompanying conventional electronic circuitry (not shown).

Probe 10 further includes a means for receiving an ultrasonic signal. The receiving means is another ultrasonic transducer. Most preferably, ultrasonic transducer 36 functions as both the transmitting means and the receiving means. Alternatively, the transmitting and receiving means is provided by a plurality of mini transducers arranged in a mosaic pattern and in communication with appropriate signal filtering electronics.

Probe 20 is further characterized by a means therein for reflecting a portion of the ultrasonic signal to provide a reflected ultrasonic reference signal. Preferably, void 24 hermetically sealed within probe body 20 from contact with the fluid whose characteristics are to be measured forms this means. Void 24 includes a reference reflecting surface 25 located a known distance r from transducer 36. Preferably surface 25 is proximal to transducer 36 for reflecting a portion of the ultrasonic signal. Substantially flat surface 25 is oriented in a plane perpendicular to the direction of propagation of the ultrasonic signal through probe body 20. Alternatively, void 24 is filled with any appropriate substance 26 having a density different from probe body 20. In either embodiment, the change in density at surface 25 results in a portion of the ultrasonic signal being reflected to transducer 36 to provide an internal reference signal located a known distance r from transducer 36.

Solid probe body 20 of probe 10 further includes a first surface 32 for contacting the fluid whose characteristics are to be determined. Preferably, first surface 32 is substantially flat and oriented in a plane substantially perpendicular to the direction of propagation of the ultrasonic signal. The change in density between solid probe body 20 and the fluid whose characteristics are to be determined at surface 32 provides a reflecting surface from which a portion of the ultrasonic signal is reflected to transducer 36 producing a first sample signal. Measurement of the signals reflected from reference surface 25 and first reflecting surface 32 provides information useful in determining certain fluid characteristics, such as reflectance, impedance and the like.

In another embodiment of the present invention useful in determining the density of a fluid, solid probe body 20 of probe 10 further includes a second surface 34 for contacting the fluid to provide a second reflected ultrasonic fluid signal. Preferably surface 34 is similar to surface 32, being substantially flat and oriented substantially perpendicular to the direction of propagation of the ultrasonic signal. Surfaces 32 and 34 are located on opposite sides of gap 30. Although gap 30 is illustrated as open, it is also contemplated that gap 30 may be enclosed. Gap 30 may be located in any appropriate fluid receiving or conduit means, e.g., circular, oval, elongate or square tubing or the like. Gap 30 is suitable for receiving therein the fluid whose characteristics are to be determined. The fluid within gap 30 may be either static or dynamic. Surfaces 32 and 34 are located a known distance s apart. Although surfaces 32 and 34 are preferably parallel and substantially flat, it is contemplated that any appropriately shaped reflecting surface providing sufficiently strong and differentiated reflected ultrasonic signals to the receiving transducer may be employed.

It is also contemplated that a device in accord with the present invention may be constructed integrally with a drill collar or the like for use in a downhole environment. In one embodiment of such a device, the fluid receiving means comprises a groove of appropriate size cut into the outer surface of the drill collar, preferably longitudinally with respect to the drill collar. A slanted helical groove cut about the outer surface of the drill collar to guide the fluid flow through the gap provides the most preferably open arrangement. Alternatively, a portion or all of the fluid receiving means is in the form of a conduit, e.g., circular or oval tubing, to provide a more sheltered fluid path.

In order to minimize the interference from secondary and higher order reflections, it is desirable that the distance s be less than the product of the distance r with the ratio of the speed of sound in the fluid present in gap 30 to the speed of sound in solid body 20 of probe 10.

$$s < r \cdot c_f / c_s$$

Figure 3:
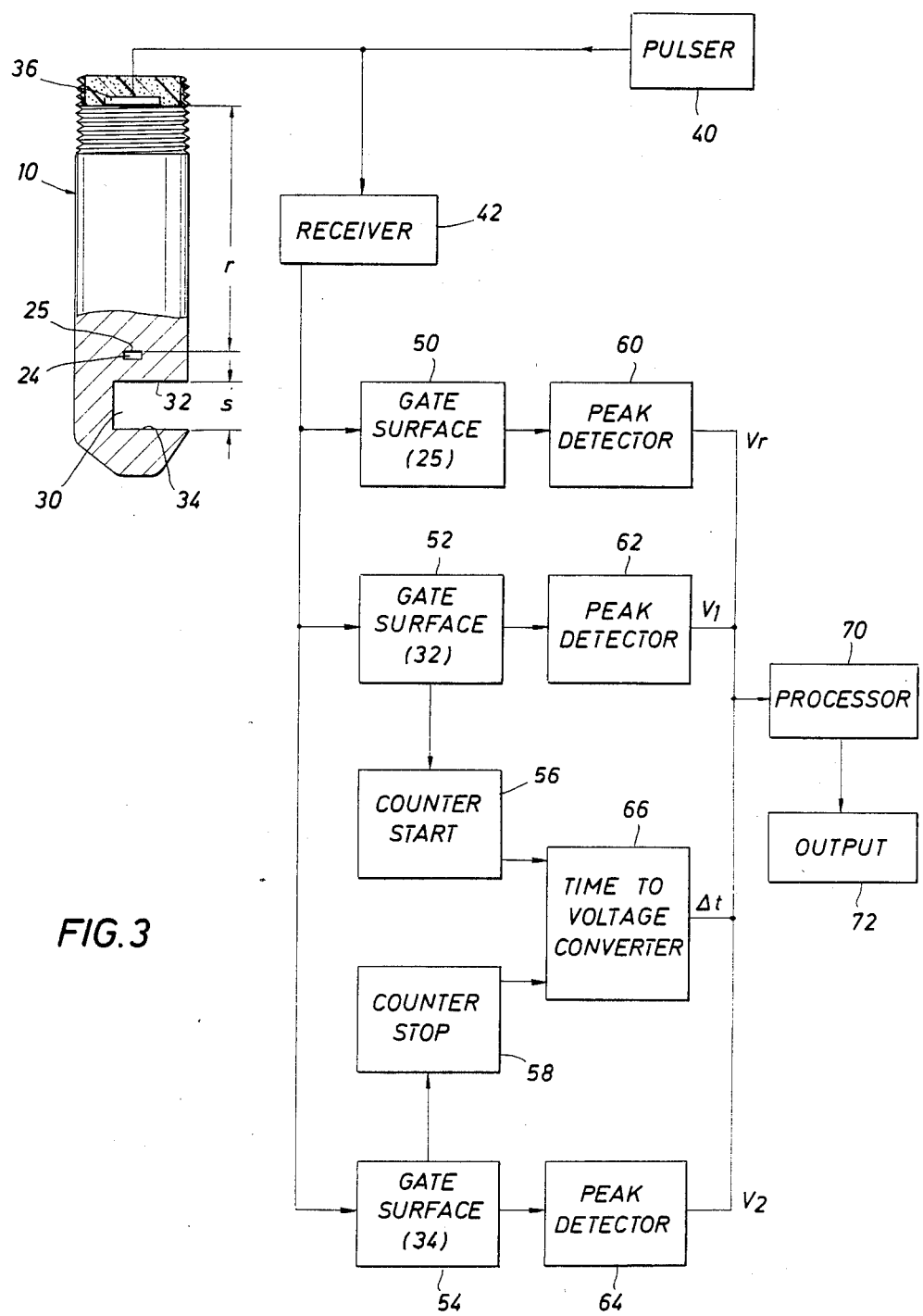
FIG. 3 is a block diagram of a probe and associated electronic circuitry in accordance with the present invention.

FIG. 3 illustrates schematically a probe and associated circuitry in accordance with the present invention. The device of the present invention further includes a receiver amplifier 42 of conventional electronic configuration and means for gating the signals received from each reflecting surface. FIG. 3 schematically illustrates separate gating means 50, 52 and 54 associated respectively with the signals received from surfaces 25, 32 and 34. Means for measuring the amplitude of the first half-cycle of each reflected ultrasonic signal comprises conventional peak detectors 60, 62 and 64 associated with the signals reflected respectively from surfaces 25, 32 and 34. To determine the density of the fluid in gap 30, it is necessary to determine the signal travel time in the fluid in gap 30. This time is obtained using a conventional counter and time-to-voltage converter 66, initiated by count starter 56 in conjunction with gating means 52 and terminated by count stop 58 in conjunction with gating means 54. The signals received are transmitted to conventional electronic processor 70 having output means 72. In the contemplated use of probe 10 to measure density and other fluid characteristics in a downhole drilling operation, processor 70 may be located at the surface to provide an easily readable output for the drilling operator.

The method of the present invention comprises contacting a fluid whose characteristics are to be determined with a first fluid reflecting surface 32 of a solid probe 10, transmitting an ultrasonic signal into solid probe 10 by a transmitting means such as transducer 36. Solid probe 10 includes therein hermetically sealed from the fluid a means, such as surface 25, for reflecting a portion of the signal to produce a reference signal. The method further includes receiving the reflected ultrasonic signals from surfaces 25 and 32 with a receiving means, such as transducer 36. A further embodiment of the present invention includes contacting the fluid with a second reflecting surface 34 of probe 10 and receiving at transducer 36 signals reflected from this second surface. The method further contemplates the gating of the received signals so that only the first half-cycle of each reflected signal is received, the measuring of the magnitude of the first half-cycle of each gated signal and the time delay between the receipt of signals reflected from the first and second fluid reflecting surfaces 32 and 34. Finally, the reflected reference signal may be used to normalize the magnitudes of the reflected sample signals to eliminate errors in determination of absolute measurements.

Figure 2:
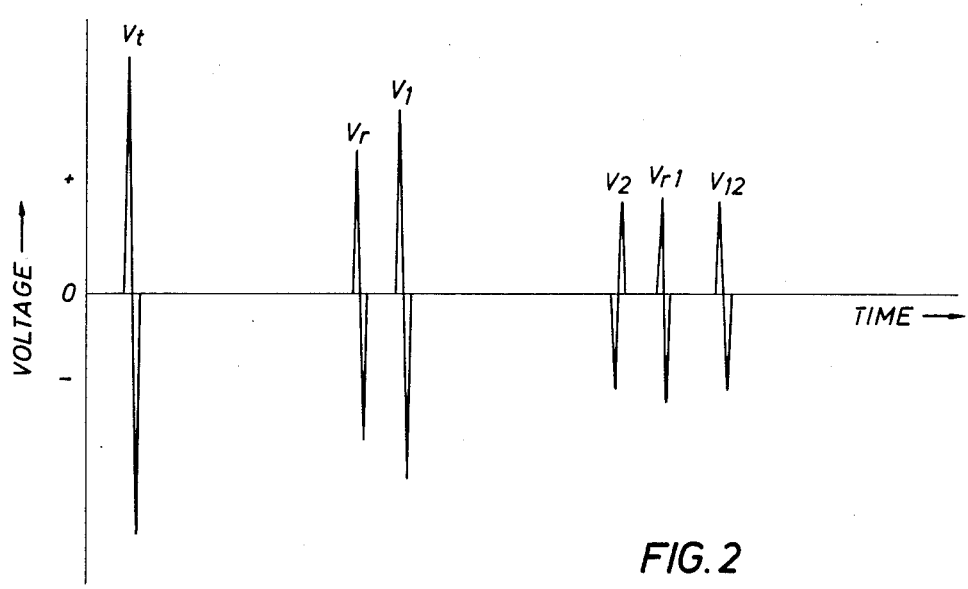
FIG. 2 is a graphical representation of the measurement of the reflected voltage of the first full cycle reflected from each surface plotted versus time.

In operation, an ultrasonic wave is transmitted from transducer 36 through solid body 20 of probe 10 toward reference reflector surface 25 and on toward the solid/fluid interface at surface 32 and then at surface 34. A portion of the wave is reflected at 25. A further portion of the wave is reflected at 32 and a portion transmitted into and through the fluid in gap 30. The wave in the fluid is reflected at surface 34. FIG. 2 illustrates the relationship of the transmitted wave, $V_t$, to the waves reflected and received from surfaces 25, 32 and 34, respectively denoted as $V_r$, $V_1$ and $V_2$. FIG. 2 further illustrates the secondary reflections received from surfaces 25 and 32.

A probe constructed in accordance with the present invention is useful in the determination of various fluid characteristics, examples of which are discussed hereinafter for illustrative purposes only. An ultrasonic wave transmitted from transducer 36 into solid probe body 10 encounters reference reflector surface 25 from which a portion of the wave is reflected and received by transducer 36. A further portion of the wave proceeds to solid/fluid interface 32 from which a portion thereof is reflected and received by transducer 36. The reflection from surface 32 measures the reflectance R from which the acoustic impedance $Z_f$ of the fluid may be determined. A still further portion of the ultrasonic wave is transmitted through the fluid in gap 30 to fluid/solid interface 34 from which a portion thereof is reflected and received by transducer 36. The additional reflection from surface 34 is required to determine the speed of sound $c_f$ and attenuation $Y_f$ in the fluid and the density $\rho_f$, compressibility $K_f$ and viscosity $\eta_f$ of the fluid.

The ratio of the peak amplitude $V_1$ from the solid/fluid interface 32 divided by the peak amplitude $V_v$ from the wave reflected from surface 32 in a vacuum is defined as the reflectance R. For a solid having density $\rho_s$ with the speed of sound $c_s$ therein, the acoustic impedance is $$Z_s = \rho_s \cdot c_s \tag{1}$$

The acoustic impedance $Z_f$ of a fluid is similarly related to the fluid density $\rho_f$ and the speed of sound $c_f$ in the fluid.

The fluid density of a viscous fluid is represented as:

$$\rho_f = \frac{\rho_s c_s}{c_f} \left[ \frac{1-R}{1+R} \right] \left[ \frac{1 + Y_f^2(1+R)^2}{4R} \right] \tag{2}$$

where $c_f$ is the speed of sound in the fluid and the attenuation factor of the fluid, $y_f \ll 1$, arises from viscous effects. The acoustic impedance $c_f$ of the fluid is determined from equation (2) where $y_f \ll 1$ to be approximately:

$$Z_f = \rho_f c_f \approx \rho_s c_s (1-R)/(1+R) \quad (2A)$$

Accordingly, the acoustic impedance $Z_f$ of the fluid is determined merely from the known acoustic impedance $Z_s$ of the solid and the reflectance R from surface 32.

In operation, transducer 36 is excited with a voltage pulse from pulser 40 to emit a stress wave. After transmitting a pulse, piezoelectric transducer 36 receives echoes from each reflecting surface 25, 32 and 34. The typical voltage signals illustrated in FIG. 2 represent the signals associated with the original transmitted signal $V_t$ and the echoes received from surfaces 25, 32 and 34 as $V_r$, $V_1$ and $V_2$. The speed of sound $c_f$ in the fluid is obviously determined from the distance s and the time delay between the echoes received as $V_1$ and $V_2$ as $c_f = 2s/\Delta t$. The reference reflector spacing r and the gap s are preferably related by $s < r \cdot c_f/c_s$ to minimize interference of the second reverberations $V_{r2}$ and $V_{12}$ with interpretation of the echo $V_2$.

The calibration reflector surface 25 is hermetically sealed from the fluid, thereby providing a reference voltage to compensate for variations in the amplitude of the transmitted wave. All voltages are normalized relative to the signal from calibration surface 25. The normalized reflectance is:

$$R = \frac{V_1(\text{fluid})/V_r(\text{fluid})}{V_1(\text{vacuum})/V_r(\text{vacuum})} \quad (3)$$

The vacuum measurements are calibrations made prior to installation with no fluids in the gap.

To avoid compensating for beam divergence, the attenuation is most conveniently obtained relative to the attenuation of water. The attenuation factor Y is:

$$Y = \frac{c_f}{2\pi f}\left[\alpha_w + \frac{\ln}{s}\left[\frac{R_f(1-R_f^2)}{V_2(\text{fluid})/V_r(\text{fluid})} \cdot \frac{V_2(\text{water})/V_r(\text{water})}{R_w(1-R_w^2)}\right]\right] \quad (4)$$

where $\alpha_w$ = attenuation of water (a small value which is determined independently) and $R_f$ and $R_w$ are the reflectances for the unknown fluid and water, respectively. The water measurements are calibrations made prior to installation with water in the gap.

A conventional electronic circuit performs the processing of the data. FIG. 3 illustrates with a block diagram an electronic system suitable for determining fluid density $\rho_f$. The system includes pulser 40 for generating a voltage pulse to excite transducer 36, receiver amplifier 42 for amplifying the received echoes, three gated peak detectors 52, 54 and 56 and a timer 66 to measure the acoustic travel time $\Delta t$ in fluid gap s from which the speed of sound $c_f$ in the fluid is determined.

The processor 70, e.g., a microprocessor programmed to store calibration data and to operate the pulser 42 and data accumulator devices 50–66 described above, calculates the reflectance R, acoustic impedance $Z_f$, speed of sound $c_f$, density $\rho_f$ and attenuation $Y_f$ using Equations 1 to 4 above. Further, the compressibility K is calculated as:

$$K = (\rho_f c_f^2)_{-1} \quad (5)$$

If the attenuation is produced strictly from viscous effects, the viscosity is estimated from the system using the expression:

$$\eta + \frac{\eta^1}{2} = \frac{\eta Y \rho_f c_f^2}{2\pi f} \quad (6)$$

where $\eta$ = shear viscosity and $\eta^1$ = dilatational viscosity. The minimum frequency f for the ultrasonic signal for validity of equation (6) may be represented as about:

$$f \approx 0.1 \frac{\rho_f c_f^2}{2\pi\left(\eta + \frac{\eta^1}{2}\right)} \quad (7)$$

The foregoing description of the invention has been directed primarily to a particular preferred embodiment in accordance with the requirements of the patent statutes and for purposes of explanation and illustration. It will be apparent, however, to those skilled in the art that many modifications and changes in the specifically described and illustrated apparatus and method may be made without departing from the scope and spirit of the invention. For example, while the disclosure of the system has been described primarily with regard to a probe useful in determining the density of a dynamic fluid in a remote location such as a borehole, it will be appreciated that a probe having either one or two solid/fluid reflecting surfaces may be employed to determine various fluid characteristics under any remote static or dynamic conditions. Therefore, the invention is not restricted to the particular form of construction illustrated and described, but covers all modifications which may fall within the scope of the following claims.

It is Applicants' intention in the following claims to cover such modifications and variations as fall within the true spirit and scope of the invention.

What is claimed is:

1. A device suitable for use in an apparatus for measuring fluid characteristics, comprising:
    a solid probe;
    means in contact with said probe for transmitting and receiving ultrasonic signals through said probe;
    means within said probe for contacting a fluid whose characteristics are to be measured with first and second surfaces on said probe capable of reflecting a portion of said ultrasonic signals to produce measurable reflected signals at said receiving means; and
    means within said probe for providing a reference signal by reflecting a portion of said ultrasonic signals, said reference reflector means located between said transmitting/receiving means and said fluid contacting means.

2. The device of claim 1 wherein said first and second reflecting surfaces are essentially parallel to one another and are essentially perpendicular to the direction of propagation of said ultrasonic signals.

3. The device of claim 2 wherein the separation of said first and second reflecting surfaces is less than the product of the separation of said transmitting/receiving means from said means for providing a reflected reference signal and the ratio of the speed of sound in said fluid in said fluid receiving means to the speed of sound in the solid of said probe.

4. The device of claim 1 wherein said fluid contacting means is a conduit through which said fluid may flow and wherein said first and second reflecting surfaces are portions of the interior wall of said conduit.

5. The device of claim 4 wherein the walls of said conduit are integral with said solid probe.

6. The device of claim 1 wherein said means for providing a reflected reference signal is a void in said solid probe.

7. The device of claim 6 wherein said void is characterized by a reflecting surface proximal said transmitting/receiving means, said surface essentially parallel to said transmitting/receiving means and essentially perpendicular to the direction of propagation of said ultrasonic signals.

8. The device of claim 6 wherein said void contains a material having a density different from the density of said solid probe.

9. The device of claim 1 wherein said reference reflector means is sealed from contact with said fluid.

10. The device of claim 1 wherein said device is incorporated in a tubular member suitable for use in a downhole environment and wherein said fluid contacting means is in fluid communication with the exterior surface of said tubular member.

11. The device of claim 10 wherein said first and second surfaces comprise opposed portions of the sides of a groove extending longitudinally along the exterior surface of said tubular member.

12. The device of claim 10 wherein said first and second surfaces comprise opposed portions of the sides of a groove extending helically about the exterior of said tubular member.

13. The device of claim 1, further including electronic circuitry for processing the received signals, comprising:
means for grating said ultrasonic signals reflected from said reference reflector means and each of said first and second reflecting surfaces of said fluid receiving means;
means for separately measuring the first half-cycle of said ultrasonic signals reflected from said reference reflector means and each of said first and second reflecting surfaces of said fluid receiving means; and
means for determining the travel time of said ultrasonic signals in said fluid between said first and second reflecting surfaces.

14. A device suitable for use in an apparatus for measuring characteristics of a fluid, comprising:
a solid probe;
means for transmitting ultrasonic signals through said probe;
means within said probe sealed from said fluid for reflecting a portion of said ultrasonic signals to provide a reflected ultrasonic reference signal;
a first surface of said probe for contacting said fluid and capable of providing at a receiving means a measurable first reflected ultrasonic fluid signal through said probe; and
means for receiving said reflected ultrsonic signals through said probe.

15. The device of claim 14 wherein said solid probe further includes a second surface for contacting said fluid and capable of providing at said receiving means a measurable second reflected ultrasonic fluid signal.

16. The device of claim 15 wherein said first and second surfaces comprise two portions of the walls of a means for contacting said fluid.

17. The device of claim 14 wherein said means for transmitting and receiving ultrasonic signals comprise a single transmitting/receiving means.

18. The device of claim 17 wherein said transmitting/receiving means is an ultrasonic transducer.

19. A method of measuring acoustic impedance of a fluid, comprising:
contacting said fluid with a first fluid reflecting surface of a solid probe,
said solid probe containing a means sealed from said fluid for reflecting a portion of said signal to produce a measurable reference signal;
transmitting ultrasonic signals into said solid probe;
receiving ultrasonic signals reflected from said reference reflecting means and from the interface of said first fluid reflecting surface and said fluid;
measuring the peak amplitude of each of said reflected signals to determine the reflectance at said interface; and
determining the acoustic impedance of said fluid from said reflectance and predetermined values of the reflectance from said first surface in a vacuum and the acoustic impedance of said solid probe.

20. The method of claim 19 for measuring at least one of the speed of sound or attenuation in said fluid or the density, compressibility or viscosity of said fluid further comprising:
contacting said fluid with a second fluid reflecting surface of said solid probe, said second surface disposed so that a portion of said transmitted signals pass a known distance through said fluid between said first and second surfaces;
receiving ultrasonic signals reflected from the interface of said second fluid reflecting surface and said fluid;
measuring the time delay between receipt of the signals reflected from said first and second fluid reflecting surfaces; and
determining at least one of the speed of sound or attenuation in said fluid or the density, compressibility or viscosity of said fluid from said reflectance, said time delay and predetermined values of the reflectance from said first surface in a vacuum and in water, the acoustic impedance of said solid probe, the attenuation of water, the frequency of said ultrasonic signal and the known distance between said first and second reflecting surfaces.

21. A method of measuring at least one of the speed of sound or attenuation in fluid or the acoustic impedance, density, compressibility or viscosiy of a fluid, comprising:
locating a fluid between first and second reflecting surfaces of a gap in a solid probe in ultrasonic communication with a means for transmitting and receiving an ultrasonic signal and including a means sealed in said probe from said fluid for providing a reflected reference signal;
transmitting an ultrasonic signal through said probe in the direction of said reflecting surfaces and said means for providing a reflected reference signal;
receiving first said reflected reference signal;
receiving second ultrasonic signals reflected at the interface of said fluid with said first surface;
receiving third ultrasonic signals reflected at the interface of said fluid with said second surface;

measuring the peak amplitude of said reflected signals to determine the reflectance at said first surface;

measuring the time delay between receipt of the signals reflected from said first and second fluid reflecting surfaces; and determining at least one of the speed of sound or attenuation in said fluid or the density, compressibility or viscosity of said fluid from said reflectance, said time delay and predetermined values of the reflectance from said first surface in a vacuum and water, the acoustic impedance of said solid probe, the attenuation of water, the frequency of said ultrasonic signal and the known distance between said first and second reflecting surfaces.

* * * * *